US008450088B2

(12) United States Patent
Hamamoto et al.

(10) Patent No.: US 8,450,088 B2
(45) Date of Patent: May 28, 2013

(54) PROCESS FOR PRODUCING CMP-N-ACETYLNEURAMINIC ACID

(75) Inventors: Tomoki Hamamoto, Sapporo (JP); Kuniaki Nagaoka, Choshi (JP); Toshitada Noguchi, Choshi (JP)

(73) Assignee: Yamasa Corporation, Chiba (JP)

( * ) Notice: Subject to any disclaimer, the term of this patent is extended or adjusted under 35 U.S.C. 154(b) by 813 days.

(21) Appl. No.: 10/573,385

(22) PCT Filed: Sep. 21, 2004

(86) PCT No.: PCT/JP2004/013760
§ 371 (c)(1),
(2), (4) Date: May 7, 2007

(87) PCT Pub. No.: WO2005/030974
PCT Pub. Date: Apr. 7, 2005

(65) Prior Publication Data
US 2008/0070285 A1 Mar. 20, 2008

(30) Foreign Application Priority Data
Sep. 26, 2003 (JP) ................................. 2003-334484

(51) Int. Cl.
*C12P 19/02* (2006.01)
*C12P 1/00* (2006.01)
*C07H 1/00* (2006.01)
*C07H 19/10* (2006.01)

(52) U.S. Cl.
USPC ................. 435/105; 435/41; 435/42; 435/84; 536/1.11; 536/26.8

(58) Field of Classification Search
CPC .............................. C12P 19/305; C12P 19/385
USPC ............... 435/7.1, 41, 42, 84, 105; 536/1.11, 536/26.8
See application file for complete search history.

(56) References Cited

U.S. PATENT DOCUMENTS

| 5,071,750 | A |   | 12/1991 | Kragl et al. |
| 5,334,514 | A | * | 8/1994 | Kittelmann et al. ............. 435/84 |
| 5,811,539 | A |   | 9/1998 | Seiffert-Stoeriko et al. |
| 5,876,980 | A |   | 3/1999 | DeFrees et al. |
| 5,922,577 | A | * | 7/1999 | Defrees et al. ................... 435/84 |
| 5,945,314 | A | * | 8/1999 | Prieto et al. ..................... 435/101 |
| 6,332,026 | B1 |  | 12/2001 | Kuusama et al. |

FOREIGN PATENT DOCUMENTS

| EP | 0 428 947 A1 | 5/1991 |
| EP | 0 524 143 A1 | 1/1993 |
| EP | 0 704 536 A1 | 7/1996 |
| JP | 61-180719 A | 8/1986 |
| JP | 02-177891 | 7/1990 |
| JP | 2003-093091 | 4/2003 |
| WO | 96/32492 A1 | 10/1996 |
| WO | 98/06239 A1 | 2/1998 |

OTHER PUBLICATIONS

Simon et al. JACS, 1988, vol. 110, pp. 7159-7163.*
Vann et al. vol. 262, No. 36, Issue of Dec. 25, 1987. pp. 17556-17562.*
Warren et al. vol. 237, No. 11, Nov. 1962, pp. 3527-3534.*
International Search Report issued Dec. 28, 2004 in the International (PCT) Application (PCT/JP2004/013760).
International Search Report issued Mar. 11, 2003 in copending U.S. Appl. No. 10/521,476.
S.L. Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives," Glycobiology (1991) vol. 1, No. 2, pp. 187 to 191.
P.J. O'Brien et al., "Functional interrelationships in the alkaline phosphatase superfamily: phosphodiesterase activity of *Escherichia coli* alkaline phosphatase," Biochemistry (2001) vol. 40, No. 19, pp. 5691 to 5699.
M.A. Nesmeyanova et al., "Multiple forms of alkaline phosphatase from *Escherichia coli* cells with repressed and derepressed biosynthesis of the enzyme," J. Bacteriol (1981) vol. 146, No. 2, pp. 453 to 459.
B. Magnouloux-Blanc et al., "Overproduction and excretion of β-lactamase and alkaline phosphatase by *Escherichia coli* olp mutants," Appl. Microbiol. Biotechnol. (1988) vol. 29, No. 2/3, pp. 258 to 263.
K. Ikeda et al., "Synthesis of sialic acid-containing nucleotide sugars: CMP-sialic acid analogs," Carbohydrate Research (1992) vol. 224, No. 7, pp. 123 to 131.
E. Simon et al., "Synthesis of CMP-NeuAc from N-Acetylglucosamine: Generation of CTP from CMP Using Adenylate Kinase," J. Am. Chem. Soc., (1988) vol. 110, pp. 7159-7163.
K. Ishige et al., "Novel Method for Enzymatic Synthesis of CMP-NeuAc", Biosci. Biotechnol. Biochem., Aug. 2001, vol. 65, No. 8, pp. 1736 to 1740.
M. Kittelmann et al., "CMP-N-acetyl neuraminic-acid synthetase from *Escherichia coli*: fermentative production and application for the preparative synthesis of CMP-neuraminic acid", Appl. Microbiol. Biotechnol., Dec. 1995, vol. 44, pp. 59 to 67.
Proceedings of 2001 Annual Conference of the Society of Biotechnology Proceedings, Japan, with English Translation.
Supplementary European Search Report issued Jun. 1, 2011 in corresponding European Application No. 04 78 7943.

* cited by examiner

*Primary Examiner* — Janet Epps-Smith
(74) *Attorney, Agent, or Firm* — Wenderoth, Lind & Ponack, L.L.P.

(57) ABSTRACT

A method by which high-purity CMP-N-acetylneuraminic acid (HPLC purity, 95% or higher), which has been difficult to obtain with any technique other than chromatography, can be easily obtained in satisfactory yield by a simple operation without the need of chromatography. The process, which is for producing high-purity CMP-N-acetylneuraminic acid (CMP-NeuAc), is characterized by conducting a suitable combination of the following steps (1) to (4). Step 1: a step in which divalent cations are added to a solution containing CMP-NeuAc to thereby precipitate the phosphoric acid, pyrophosphoric acid, and nucleotide which coexist; Step 2: a step in which a phosphatase is added to a solution containing CMP-NeuAc to thereby convert the coexistent nucleotide into nucleoside; Step 3: a step in which an organic solvent is added to precipitate the CMP-NeuAc; and Step 4: a step in which the CMP-NeuAc precipitated is recovered.

3 Claims, No Drawings

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Primer sequence for amplification of neuA gene

<400> SEQUENCE: 1
tgccatggtg aaaataataa tgacaagaa                                     19

<210> SEQ ID NO 2
<211> LENGTH: 18
<212> TYPE: DNA
<213> ORGANISM: Artificial Sequence
<220> FEATURE:
<223> OTHER INFORMATION: Primer sequence for amplification of neuA gene

<400> SEQUENCE: 2
aactgcagtg cagatcaaaa gtgcggcc                                      18

<210> SEQ ID NO 3
<211> LENGTH: 32
<212> TYPE: DNA
<213> ORGANISM: Artificial Sequence
<220> FEATURE:
<223> OTHER INFORMATION: Primer sequence for amplification of phoA gene

<400> SEQUENCE: 3
aaggatccag ctgtcataaa gttgtcacgg cc                                 32

<210> SEQ ID NO 4
<211> LENGTH: 34
<212> TYPE: DNA
<213> ORGANISM: Artificial Sequence
<220> FEATURE:
<223> OTHER INFORMATION: Primer sequence for amplification of phoA gene

<400> SEQUENCE: 4
ttctgcagcc cgtgatctgc cattaagtct ggtt                               34

PROCESS FOR PRODUCING CMP-N-ACETYLNEURAMINIC ACID

This application is a U.S. national stage of International Application No. PCT/JP2004/013760 filed Sep. 21, 2004.

TECHNICAL FIELD

The present invention relates to a process for producing CMP-N-acetylneuraminic acid (CMP-NeuAc), which is an important material for synthesizing sugar chains.

BACKGROUND ART

In recent years, with the rapid progress of research concerning the structures and functions of sugar chains, research efforts have been undertaken to develop applications of oligosaccharides, glycolipids, glycoproteins, and similar materials having physiological activities in the fields of drugs and functional materials. Among sugar chains, a sialic-acid-containing sugar chain having N-acetylneuraminic acid (NeuAc) at an end thereof is known to play an important role as a receptor in, for example, cell adhesion or viral infection.

Generally, the sialic-acid-containing sugar chain is synthesized by use of sialyltransferase as a catalyst. Sialyltransferase is an enzyme which catalyzes the transfer of sialic acid from cytidine-5'-monophosphate-N-acetylneuraminic acid (CMP-NeuAc), which serves as a sugar donor, to a sugar chain serving as an acceptor.

Basically, CMP-NeuAc is synthesized from cytidine 5'-triphosphate (5'-CTP) and neuraminic acid (NeuAc) serving as substrates by use of CMP-NeuAc synthase serving as a catalyst.

However, CMP-NeuAc, which is employed as a sugar donor, is very unstable and is difficult to prepare in large amounts. Therefore, CMP-NeuAc is very expensive and has been provided in such small amounts that would be good for reagent uses. Meanwhile, the CMP-NeuAc products currently in supply have a low purity (typically, a purity of 90% or thereabouts as determined by HPLC), since a highly pure product having a purity of 95% or more has conventionally been difficult to produce. Such a low purity inevitably renders CMP-NeuAc inappropriate as a raw material for producing a sialic-acid-containing sugar chain or a similar product.

According to a conventionally favored CMP-NeuAc purification process, cytidine 5'-monophosphate (5'-CMP), cytidine 5'-diphosphate (5'-CDP), and 5'-CTP—which are generated through degradation during reaction for producing CMP-NeuAc or during subsequent purification steps, or remain in the synthesis reaction mixture, and which are very difficult to separate from CMP-NeuAc—are all converted into cytidine compounds through removal of phosphate moieties from 5'-CMP, 5'-CDP, and 5'-CTP, which coexist with CMP-NeuAc, by use of calf-derived alkaline phosphatase (CIAP); and subsequently CMP-NeuAc is separated from the resultant cytidine compounds through chromatography treatment, such as ion-exchange chromatography or gel filtration chromatography (Patent Documents 1 to 3 and Non-Patent Document 1).

Patent Document 1: JP-A-H5-276973
Patent Document 2: JP-B-H5-73391
Patent Document 3: JP-A-H8-73480
Non-Patent Document 1: J. Am. Chem. Soc., 110, 7159-7163 (1988)

DISCLOSURE OF THE INVENTION

Problems to be Solved by the Invention

However, the aforementioned conventional processes require a chromatography treatment, which leads to an increase in production time and cost, and thus are not necessarily suitable for purification of CMP-NeuAc during mass production thereof on an industrial scale. Meanwhile, calf-derived alkaline phosphatase (CIAP), which is employed for the aforementioned phosphate treatment, is currently difficult to prepare in large amounts, and thus demand has arisen for a process employing a phosphatase other than CIAP.

Also, there has been reported a fractional precipitation process utilizing the difference in solubility to a solvent, which process requires no chromatography treatment (J. Am. Chem. Soc., 110, 7159-7163 (1988)). However, the fractional precipitation process is far inferior to the aforementioned chromatography treatment process in terms of the percent collection and purity of CMP-NeuAc, and thus has not yet been put into practice.

Means for Solving the Problems

The present inventors have conducted extensive studies on a process for mass-producing highly pure CMP-NeuAc at high yield without requirement for any chromatography treatment, and as a result have found that, among others, (1) when a divalent cationic species capable of forming insoluble precipitates with phosphoric acid, such as $Ca^{2+}$ or $Mn^{2+}$, is added immediately after completion of catalytic reaction by use of CMP-NeuAc synthase, inorganic phosphoric acid and pyrophosphoric acid which are contained in the resultant reaction mixture can be precipitated in the form of phosphoric acid salt, and 5'-CTP (i.e., an unreacted substrate) can also be precipitated in salt form; (2) addition of such a divalent cationic species has no effect at all on phosphatase reaction, and 5'-CMP, 5'-CDP, and 5'-CTP can be specifically degraded into cytidine; and (3) addition of such a divalent cationic species enhances, in a solvent-selective manner, precipitation of CMP-NeuAc in an alcohol or a similar organic solvent, and CMP-NeuAc is very easily precipitated separately from cytidine and NeuAc. The present invention has been accomplished on the basis of these findings.

Accordingly, the present invention provides the following.

(1) A process for producing highly pure CMP-NeuAc, comprising the following steps 1 to 4:

step 1: a step of adding a divalent cationic species to a CMP-NeuAc-containing solution, thereby causing phosphoric acid, pyrophosphoric acid, and a nucleotide which coexist with CMP-NeuAc to precipitate;

step 2: a step of adding a phosphatase to the CMP-NeuAc-containing solution, thereby converting the nucleotide which coexists with CMP-NeuAc into a nucleoside;

step 3: a step of adding an organic solvent, thereby precipitating CMP-NeuAc in the form of salt; and step 4: a step of collecting the thus-precipitated CMP-NeuAc, wherein these steps are performed in a predetermined combination.

(2) A process as described in (1) above, wherein these steps are performed in the following sequence: step 1, step 2, step 3, and then step 4.

(3) A process as described in (1) above, wherein these steps are performed in the following sequence: step 2, step 1, step 3, and then step 4.

(4) A process as described in (1) above, wherein step 1 and step 2 are performed simultaneously.

(5) A process as described in (1) above, wherein step 3 and step 4 are performed a plurality of times.

(6) A process as described in any of (1) to (5) above, wherein the divalent cationic species is a calcium ion or a manganese ion.

(7) A process as described in any of (1) to (5) above, wherein the phosphatase is *Escherichia coli* alkaline phosphatase.

(8) A process as described in any of (1) to (5) above, wherein the organic solvent is an alcohol having a carbon number of 5 or less.

(9) A production process as described in (1) above, wherein the CMP-NeuAc collected in step 4 is subjected to cation exchange reaction for substitution of the cationic moiety of the CMP-NeuAc.

(10) A production process as described in (9) above, wherein the cation exchange reaction employs an ion-exchange resin.

Effects of the Invention

According to the present invention, highly pure CMP-NeuAc (HPLC purity: 95% or more), which has been difficult to obtain through a technique other than chromatography treatment, can be easily obtained at high yield through a simple procedure without employment of any chromatography treatment.

BEST MODE FOR CARRYING OUT THE INVENTION

As described above, the CMP-NeuAc production process of the present invention is based on steps 1 to 4. These steps will next be described in detail.

(Step 1)

In step 1, a divalent cationic species is added to a CMP-NeuAc-containing solution, to thereby cause phosphoric acid, pyrophosphoric acid, and a nucleotide which coexist with CMP-NeuAc to precipitate.

No particular limitation is imposed on the CMP-NeuAc-containing solution to be provided to step 1 (or step 2), so long as the solution is an aqueous solution containing CMP-NeuAc. For example, the CMP-NeuAc-containing solution may be a reaction mixture obtained through CMP-NeuAc synthesis by use of an enzyme. Specific examples of the CMP-NeuAc-containing solution include a solution containing CMP-NeuAc synthesized from 5'-CTP and NeuAc serving as substrates by use of CMP-NeuAc synthase serving as a catalyst.

No particular limitation is imposed on the divalent cationic species to be added, so long as it can form insoluble precipitates with inorganic phosphoric acid, pyrophosphoric acid, or a nucleotide. Examples of the divalent cationic species include a calcium ion and a manganese ion. Specifically, in the case where calcium ion is desired to be added, there may be employed a water-soluble calcium salt, such as calcium chloride, calcium sulfate, calcium hydroxide, or calcium carbonate; whereas in the case where manganese ion is desired to be added, there may be employed a water-soluble manganese salt, such as manganese chloride or manganese sulfate. The amount of the divalent cationic species to be added may be appropriately determined so as to fall within a range of 0.1 to 2,000 mM.

When such a divalent cationic species is added to a CMP-NeuAc-containing solution, and the resultant mixture is maintained at a temperature of 0 to 60° C. with, if necessary, the pH being adjusted to 6.0 to 13.0 and/or stirring, an insoluble salt such as calcium phosphate or manganese phosphate is precipitated. The resultant precipitate is removed through generally employed solid-liquid separation means (e.g., filtration or centrifugation), followed by the subsequent step.

(Step 2)

In step 2, a phosphatase is added to the CMP-NeuAc-containing solution, to thereby convert a nucleotide which coexists with CMP-NeuAc into a nucleoside.

No particular limitation is imposed on the phosphatase to be employed for reaction, so long as it is an enzyme capable of converting a nucleotide into a nucleoside through removal of the phosphate residue of the nucleotide, and capable of specifically hydrolyzing 5'-CMP, 5'-CDP, and 5'-CTP to cytidine. However, from the viewpoint of, for example, stability of CMP-NeuAc during reaction or easy enzyme preparation, the phosphatase is preferably an alkaline phosphatase, particularly preferably *Escherichia coli* alkaline phosphatase.

The conversion reaction can be performed by adding the phosphatase to the CMP-NeuAc-containing solution in an amount of 0.01 units or more (preferably 0.1 to 50 units) on the basis of 1 mL of the solution, and allowing reaction to proceed at 70° C. or lower (preferably at 20 to 60° C.) for about 0.1 to about 50 hours with, if necessary, stirring and pH adjustment.

No particular limitation is imposed on the sequence of the aforementioned steps 1 and 2, and step 1 may be followed by step 2 or vice versa, or these steps may be performed simultaneously. For example, in the case where step 1 and step 2 are to be performed in this sequence, since the reaction mixture obtained in step 1 contains a divalent cationic species, and thus an insoluble salt such as calcium phosphate or manganese phosphate is precipitated during or after phosphatase treatment, the resultant precipitate is removed through generally employed solid-liquid separation means (e.g., filtration or centrifugation), followed by the subsequent step.

(Step 3)

In step 3, an organic solvent is added, to thereby precipitate CMP-NeuAc in the form of salt.

The organic solvent to be added is preferably an alcohol having a carbon number of 1 to 5. Specific examples of the organic solvent which may be employed include methanol, ethanol, and isopropanol. The amount of the organic solvent to be added may be appropriately determined to fall within a range of 0.1 to 20 times that of the reaction mixture.

When such an organic solvent is added to the reaction mixture obtained through treatment in the aforementioned step 1 or 2, and the resultant mixture is maintained at a temperature of −80 to 60° C. with, if necessary, pH adjustment to 6.0 to 13.0 and/or stirring, CMP-NeuAc is precipitated.

(Step 4)

In step 4, the thus-precipitated CMP-NeuAc is collected.

Collection of the CMP-NeuAc can be performed through generally employed solid-liquid separation means (e.g., filtration or centrifugation). If desired, the thus-collected CMP-NeuAc is dried, to thereby yield a final product.

When the aforementioned step 3 and step 4 are performed a plurality of times (typically, about two to about five times), CMP-NeuAc of higher purity can be produced.

(Additional Step)

After completion of the aforementioned step 4, the thus-obtained CMP-NeuAc is in the form of a salt such as a calcium salt or a manganese salt. If desired, the CMP-NeuAc salt may be converted into, for example, a sodium salt.

Cation exchange reaction can be performed through redissolution of the thus-collected precipitate, followed by, for example, bringing the resultant solution into contact with a cation-exchange resin having a target cationic species (e.g., causing the solution to pass through a column containing the resin).

The thus-produced CMP-NeuAc is a highly pure product having an HPLC purity of 95% or more, and containing a very small amount of a contaminant (e.g., 5'-CMP).

EXAMPLE

The present invention will next be described in detail by way of Examples, which should not be construed as limiting the invention thereto. Quantitation of CMP-NeuAc in a reaction mixture was carried out by means of HPLC. Specifically, an ODS-HS302 column (product of YMC) was employed for separation, and 0.1 M triethylamine-phosphoric acid (pH 6.0) was employed as an eluent.

Example 1

(1) Preparation of CMP-NeuAc Synthase

*Haemophilus influenzae* Rd strain chromosomal DNA (ATCC 51907D) was employed as a template, and the two below-described DNA primers were synthesized through a customary method. By use of the resultant primers, the CMP-NeuAc synthase (neuA) gene of *H. influenzae* was amplified through PCR.

```
Primer (A):
5'-TGCCATGGTGAAAATAATAATGACAAGAA-3'   (SEQ ID NO: 1)

Primer (B):
5'-AACTGCAGTGCAGATCAAAAGTGCGGCC-3'   (SEQ ID NO: 2)
```

Amplification of the neuA gene through PCR was performed in a DNA Thermal Cycler (product of Perkin-Elmer Cetus Instrument) by adding thereto a reaction mixture (100 µL) containing 50 mM potassium chloride, 10 mM Tris-HCl (pH 8.3), 1.5 mM magnesium chloride, 0.001% gelatin, template DNA (0.1 µg), DNA primers (A) and (B) (0.2 µM each), and AmpliTaq DNA polymerase (2.5 units). The cycling protocol consisted of 25 cycles, each including the following three steps: thermal denaturation (94° C.×1 minute), annealing (55° C.×1.5 minutes), and elongation (72° C.×3 minutes).

After gene amplification, the reaction mixture was treated with a phenol/chloroform (1:1) mixture, to thereby yield a water-soluble fraction. To the water-soluble fraction, ethanol was added in a volume twice that of the fraction, to thereby precipitate DNA. The DNA collected through precipitation was subjected to separation by means of agarose gel electrophoresis according to the method described in literature ("Molecular Cloning, A Laboratory Manual, Second Edition" (edited by Sambrook, et al., Cold Spring Harbor Laboratory, Cold Spring Harbor, N.Y. (1989))), to thereby purify DNA fragments having a size of 720 b. The DNA was cleaved with restriction enzymes NcoI and PstI, to thereby yield DNA fragments. The DNA fragments were ligated, by use of T4 DNA ligase, with plasmid pTrc99A which had likewise been digested with restriction enzymes NcoI and PstI. By use of the reaction mixture containing the thus-ligated DNA, *Escherichia coli* strain JM109 was transformed, and from the resultant ampicillin-resistant transformants, plasmid pTrcsiaBNP was isolated. pTrcsiaBNP has a structure in which a DNA fragment containing a structural gene of neuA gene has been inserted into the NcoI-PstI cleavage sites located downstream of the trc promoter of pTrc99A.

*Escherichia coli* strain JM109 harboring the plasmid pTrcsiaBNP was inoculated in a 2×YT medium (100 mL) containing 100 µg/mL ampicillin, followed by shaking culture at 37° C. When the number of cells had reached $4\times10^8$ cells/mL, IPTG was added to the culture broth so as to attain a final concentration of 0.25 mM. Shaking culture was further continued at 37° C. for six hours. After completion of culturing, the culture was subjected to centrifugation (9,000×g, 10 minutes), whereby the cells were collected. The cells were suspended in a buffer solution (5 mL) (100 mM Tris-HCl (pH 7.8), 10 mM $MgCl_2$). The cells were disrupted through ultrasonic treatment, and the resultant cell debris was removed through centrifugation (20,000×g, 10 minutes).

The thus-obtained supernatant fraction was employed as an enzyme solution, and CMP-NeuAc synthase activity was measured with this enzyme solution. The results are shown below in Table 1 together with the data from a control bacterium (*Escherichia coli* K-12 strain JM109 harboring pTrc99A). In the present invention, CMP-NeuAc synthase activity units were determined by measuring and calculating activity in relation to the synthesis of CMP-NeuAc from 5'-CTP and N-acetylneuraminic acid through the below-described method.

(Measurement of CMP-NeuAc Synthase Activity and Calculation of Units)

The CMP-NeuAc synthase was added to 50 mM Tris-HCl buffer solution (pH 8.0), 20 mM magnesium chloride, 5 mM CTP, and 10 mM N-acetylneuraminic acid, and the resultant mixture was allowed to react at 37° C. for five minutes. As a control, a cell lysate of *Escherichia coli* strain JM109 harboring pTrc99A was employed instead of CMP-NeuAc synthase and similar reaction was performed.

To the reaction mixture, 70% ethanol (twice the amount of the mixture) was added to thereby stop the reaction, and the mixture was diluted and then analyzed through HPLC. The separation process was performed by use of an HS-302 column (product of YMC) and, as an eluent, a mixture of 50 mM aqueous magnesium acetate solution and 1 mM aqueous tetrabutylammonium solution. From the results of the HPLC analysis, the amount of CMP-NeuAc contained in the reaction mixture was calculated. The activity of the synthase capable of synthesizing 1 µmole of CMP-NeuAc in one minute at 37° C. was defined as one unit, and the CMP-NeuAc synthase activity was calculated.

TABLE 1

| Bacterium/Plasmid | CMP-NeuAc synthase activity (units/mg protein) |
|---|---|
| JM109/pTrc99A | <0.01 |
| JM109/pTrcsiaBNP | 2.45 |

(2) Preparation of *Escherichia coli* Alkaline Phosphatase

Chromosomal DNA of *Escherichia coli* strain JM105 (Takara Bio Inc.) was prepared through the method of Saito and Miura (Biochemica et Biophysica Acta., 72, 619 (1963)). The chromosomal DNA was employed as a template, and the two below-described DNA primers were synthesized through a customary method. By use of the resultant primers, *Escherichia Coli* phoA gene (EMBL/GENEBANK/DDBJ DATA BANKS, Accession No. AE000145.1) was amplified through PCR.

```
Primer (C):
                                    (SEQ ID NO: 3)
5'-AAGGATCCAGCTGTCATAAAGTTGTCACGGCC-3'

Primer (D):
                                    (SEQ ID NO: 4)
5'-TTCTGCAGCCCGTGATCTGCCATTAAGTCTGGTT-3'
```

Amplification of the phoA gene through PCR was performed in a DNA Thermal Cycler (product of Perkin-Elmer Cetus Instrument) by adding thereto a reaction mixture (100 µL) containing 50 mM potassium chloride, 10 mM Tris-HCl (pH 8.3), 1.5 mM magnesium chloride, 0.001% gelatin, 0.2 mM dATP, 0.2 mM dGTP, 0.2 mM dCTP, 0.2 mM dTTP, template DNA (0.1 µg), DNA primers (C) and (D) (0.2 mM each), and AmpliTaq DNA polymerase (2.5 units). The cycling protocol consisted of 25 cycles, each including the following three steps: thermal denaturation (94° C.×1 minute), annealing (55° C.×1 minute), and elongation (72° C.×3 minutes).

After gene amplification, the reaction mixture was treated with a phenol/chloroform (1:1) mixture, to thereby yield a water-soluble fraction. To the water-soluble fraction, ethanol was added in a volume twice that of the fraction, to thereby precipitate DNA. The DNA collected through precipitation was subjected to separation by means of agarose gel electrophoresis according to the method described in literature (Molecular cloning), to thereby purify DNA fragments having a size of 1.5 kb. The DNA was cleaved with restriction enzymes BamHI and PstI, to thereby yield DNA fragments. The DNA fragments were ligated, by use of T4 DNA ligase, with plasmid pTrc99A (Pharmacia Biotech.) which had likewise been digested with restriction enzymes BamHI and PstI. By use of the reaction mixture containing the thus-ligated DNA, *Escherichia coli* strain JM109 (Takara Bio Inc.) was transformed, and from the resultant ampicillin-resistant transformants, plasmid pTrc-phoA was isolated.

pTrc-phoA has a structure in which a DNA fragment containing a *Escherichia coli* phoA structural gene and a ribosome binding site has been inserted into the BamHI-PstI cleavage sites located downstream of the trc promoter of pTrc99A.

*Escherichia coli* strain JM109 harboring the plasmid pTrc-phoA was inoculated in a 2×YT medium (500 mL) containing 100 µg/mL ampicillin, followed by shaking culture at 37° C. When the number of cells had reached 4×10$^8$ cells/mL, IPTG was added to the culture broth so as to attain a final concentration of 0.2 mM. Shaking culture was further continued at 37° C. for 22 hours. After completion of culturing, the culture was subjected to centrifugation (9,000×g, 10 minutes), whereby the cells were collected. The cells were suspended in a buffer solution (25 mL) (20 mM Tris-HCl (pH 8.0), 5 mM magnesium chloride). The cells were disrupted through ultrasonic treatment, and the resultant cell debris was removed through centrifugation (20,000×g, 10 minutes).

Subsequently, the thus-obtained supernatant fraction was thermally treated at 80° C. for 15 minutes, and then the resultant cell debris was removed through centrifugation (20,000×g, 10 minutes). The resultant product was dialyzed against a buffer solution (total: 2 L) (20 mM Tris-HCl (pH 8.0), 1 mM magnesium chloride) at 4° C. overnight, and the resultant cell debris was removed through centrifugation (20,000×g, 10 minutes).

The thus-obtained supernatant fraction was employed as an enzyme solution, and alkaline phosphatase activity was measured with the enzyme solution. The results are shown below in Table 2 together with the data from a control bacterium (*Escherichia coli* strain JM109 harboring pTrc99A). In the present invention, alkaline phosphatase activity units were measured and calculated through the below-described method.

(Measurement of Alkaline Phosphatase Activity and Calculation of Units)

The enzyme solution was added to a solution containing 400 mM Tris-HCl buffer solution (pH 8.5) and 20 mM uridine 5'-monophosphate, and the resultant mixture was allowed to react at 40° C. for 5 to 15 minutes. As a control, a cell lysate of *Escherichia coli* strain JM109 harboring pTrc99A was employed instead of alkaline phosphatase and similar reaction was performed. To the reaction mixture, 0.5 M potassium dihydrogenphosphate solution (equal to the amount of the mixture) was added to thereby stop the reaction, and then the mixture was analyzed through HPLC, to thereby determine the amount of uridine contained in the reaction mixture. The activity of the phosphatase capable of producing 1 µmole of uridine in one minute at 37° C. was defined as one unit, and the alkaline phosphatase activity was calculated.

TABLE 2

| Bacterium/Plasmid | Alkaline phosphatase activity (units/mg protein) |
|---|---|
| JM109/pTrc99A | <0.5 |
| JM109/pTrc-phoA | 14.04 |

(3) Effect of Addition of Divalent Cationic Species 0.2 M NeuAc solution (5 mL), 0.25 M CTP·3Na solution (4 mL), and 1 M magnesium chloride solution were mixed together, and the pH of the resultant mixture was adjusted to 10 with 2 M sodium hydroxide solution, followed by filling up to 50 mL with distilled water. After the mixture was heated to 40° C., CMP-NeuAc synthase (70 units) was added thereto, and reaction was initiated with stirring. During the course of reaction, 1 M sodium hydroxide solution was added dropwise as desired to the reaction mixture so as to maintain its pH at around 8.5.

One hour after initiation of the reaction, 1 M calcium chloride solution (3 mL) was added, and subsequently *Escherichia coli* alkaline phosphatase (5 units) was added, and reaction was further performed at 40° C. with stirring. During the course of reaction, 1 M sodium hydroxide solution was added dropwise as desired to the reaction mixture so as to maintain its pH at around 9.0. Thirty minutes later, an aliquot was sampled from the reaction mixture, and the composition of the reaction mixture was analyzed through HPLC. The thus-obtained results are shown below in Table 3.

Also, CMP-NeuAc synthesis was performed for one hour in a manner similar to that described above, and then 1 M manganese chloride solution (3 mL) or distilled water (3 mL) was added to the resultant reaction mixture. Thereafter, reaction with *Escherichia coli* alkaline phosphatase was performed in a manner similar to that described above, and 30 minutes later, an aliquot was sampled from the reaction mixture for analysis of the reaction mixture composition. The results are also described in Table 3.

As is clear from Table 3, addition of a divalent cationic species enables the *Escherichia coli* alkaline phosphatase reaction to be performed efficiently, and particularly enables efficient removal of CMP, which is difficult to separate from CMP-NeuAc.

TABLE 3

|  | CMP-NeuAc | CTP | CMP | Cytidine | Uridine |
|---|---|---|---|---|---|
| CaCl$_2$ | 14.57 mM | <0.02 mM | <0.02 mM | 1.283 mM | 0.7932 mM |
| MnCl$_2$ | 11.17 mM | <0.02 mM | <0.02 mM | 0.7051 mM | 0.5031 mM |
| Distilled water | 16.34 mM | 0.8625 mM | 0.8065 mM | 0.0541 mM | 0.1127 mM |

Example 2

Effect of Addition of Divalent Cationic Species on Ethanol Precipitation

CMP-NeuAc·2Na powder (product of Sigma) (70 mg) was dissolved in distilled water, to thereby prepare 500 μL of an aqueous solution (about 0.2 M solution). The aqueous solution was divided into aliquots (100 μL each), and (A) 1 M calcium chloride solution, (B) 1 M manganese chloride solution, or (C) distilled water (50 μL each) was added to any of the aliquots. Subsequently, ethanol (300 μL) was added to each of the resultant aliquots, and the mixture was allowed to stand still at 4° C. overnight. Thereafter, the mixture was subjected to centrifugation at 121,000×g and 4° C. for 10 minutes, and the absorbance of the resultant supernatant was measured at 270 nm. The percent collection of CMP-NeuAc as a precipitate fraction was calculated on the basis of the thus-obtained measurements. The results are shown in Table 4.

As is clear from Table 4, addition of a divalent cationic species capable of forming insoluble precipitates with phosphoric acid dramatically enhances the percent collection of CMP-NeuAc in ethanol precipitation treatment.

TABLE 4

|  | Percent collection in precipitation (%) |
|---|---|
| CaCl$_2$ | 89.7 |
| MnCl$_2$ | 55.4 |
| Distilled water | 0.40 |

Example 3

NeuAc (product of Marukin Chuyu Co., Ltd.) (12.4 g) and 5'-CTP·2Na (product of Yamasa Corporation) (24.2 g) were added to and dissolved in 1 M magnesium chloride solution (100 mL), and the pH of the resultant solution was adjusted to 9.5 with 1 M sodium hydroxide, followed by filling up to 2 L with distilled water. After the mixture was heated to 40° C., CMP-NeuAc synthase (2,810 units) was added thereto, and reaction was initiated with stirring. During the course of reaction, 1 M sodium hydroxide solution was added dropwise as desired to the reaction mixture so as to maintain its pH at around 8.5.

One hour after initiation of the reaction, 2.5 M calcium chloride (50 mL) was added, and subsequently *Escherichia coli* alkaline phosphatase (200 units) was added, and reaction was further performed at 40° C. with stirring. During the course of reaction, 1 M sodium hydroxide solution was added dropwise as desired to the reaction mixture so as to maintain its pH at around 9.0.

One hour after the phosphatase reaction, the resultant reaction mixture was cooled to 4° C. After being allowed to stand overnight, the reaction mixture was subjected to centrifugation (15,000×g, 15 minutes) for removal of precipitates. The pH of the resultant supernatant was adjusted to 7.0 with 1 M hydrogen chloride solution, and then carbon powder (2 g) was added to the resultant mixture, followed by stirring in ice for one hour. After the carbon powder was removed by means of a 0.45 μm filter, the resultant filtrate (2.03 L) was concentrated to about 100 mL by use of an evaporator.

The precipitates generated during the course of concentration were removed by means of a G3 glass filter, and subsequently ethanol (660 mL) was added to the resultant filtrate (140 mL), followed by stirring at room temperature. Thereafter, the mixture was further stirred at 4° C., and then allowed to stand overnight.

The resultant precipitates were collected by means of a G3 glass filter, and the thus-collected precipitates were dried under reduced pressure. The precipitates were dissolved in distilled water to prepare 150 mL of an aqueous solution. Ethanol (450 mL) was added to the aqueous solution, and the resultant mixture was stirred at room temperature. Thereafter, the mixture was further stirred at 4° C., and then allowed to stand overnight.

The resultant precipitates were collected by means of a G3 glass filter, and the thus-collected precipitates were dried under reduced pressure. The precipitates were dissolved in distilled water to prepare 250 mL of an aqueous solution. The aqueous solution was caused to pass through a column (100 mL) of a sodium-ion-substituted PK216(Na) resin (product of Mitsubishi Chemical Corporation) at a flow rate of 400 to 450 mL/h.

A CMP-NeuAc-containing fraction (370 mL) was collected, and the fraction was concentrated to about 50 mL by use of an evaporator. Thereafter, the pH of the concentrate was adjusted to 7.0 with 1 M hydrogen chloride solution.

Carbon powder (0.5 g) was added to the concentrate, and the resultant mixture was stirred in water for about one hour. Thereafter, the carbon powder was removed by means of a 0.45-μm filter. Ethanol (400 mL) was added to the resultant filtrate (70 mL), and the resultant mixture was stirred at room temperature, followed by further stirring at 4° C. overnight. The resultant precipitates were collected by means of a G3 glass filter, and the thus-collected precipitates were dried under reduced pressure, to thereby yield CMP-NeuAc·2Na powder (18.4 g) having an HPLC purity of 98.8%.

The results of HPLC analysis of the CMP-NeuAc are as follows.

<Analysis Conditions>

Column: ODS-HS302 (product of YMC)

Eluent: 0.1 M triethylamine-phosphoric acid (pH 6.0)

<Analysis Results>

CMP-NeuAc: 98.8%

5'-CMP: 1.2%

The invention claimed is:

1. A process for purification of CMP-N-acetylneuraminic acid (CMP-NeuAc), comprising the following steps (1) to (5):

step (1): a step of adding a calcium ion or a manganese ion to a CMP-NeuAc-containing solution, thereby causing phosphoric acid, pyrophosphoric acid, and a nucleotide which coexist with CMP-NeuAc to precipitate, wherein the CMP-NeuAc-containing solution is a solution obtained by catalytic reaction of cytidine 5'-triphosphate (5'-CTP) and neuraminic acid (NeuAc) by use of CMP-NeuAc synthetase as a catalyst;

step (2): a step of adding a phosphatase to the CMP-NeuAc-containing solution, thereby converting the nucleotide which coexists with CMP-NeuAc into a nucleoside;

step (3): a step of adding ethanol, thereby precipitating CMP-NeuAc in the form of salt;

step (4): a step of collecting the thus-precipitated CMP-NeuAc; and step (5): a step of subjecting the thus-collected CMP-NeuAc to cation exchange reaction by bringing the thus-collected CMP-NeuAc into contact with a cation-exchange resin, and then to a treatment with carbon powder, wherein these steps are performed in a sequence selected from:

step (1), step (2), step (3), step (4), and then step (5) or step (1) and step (2) are performed simultaneously and then steps (3), (4), and (5) are performed sequentially, and wherein the thus purified CMP-NeuAc in the form of salt has a purity measured by HPLC of 95% or more.

2. The process according to claim 1, wherein step (3) and step (4) are performed a plurality of times.

3. The process according to claim 1, wherein the phosphatase is *Escherichia coli* alkaline phosphatase.

* * * * *